United States Patent [19]

Bourguignon et al.

[11] Patent Number: 5,128,338

[45] Date of Patent: Jul. 7, 1992

[54] IMIDAZO [1,2-C] QUINAZOLINE COMPOUNDS

[75] Inventors: Jean-Jacques Bourguignon, Hipsheim; Camille-Georges Wermuth, Strasbourg; Jean-François Renaud de la Faverie, Rocquencourt le Chesnay; Catherine Thollon, Paris; Alain Lombet, Champigny, all of France

[73] Assignee: Adir et Compagnie, Courbevoie, France

[21] Appl. No.: 666,802

[22] Filed: Mar. 8, 1991

[30] Foreign Application Priority Data

Mar. 9, 1990 [FR] France .................. 90 03003

[51] Int. Cl.$^5$ .................. A61K 31/505; C07D 487/04
[52] U.S. Cl. .................. 514/233.2; 514/267; 544/115; 544/250
[58] Field of Search .................. 544/250, 115; 514/267, 514/233.2

[56] References Cited

U.S. PATENT DOCUMENTS

| 4,110,452 | 8/1978 | Rovnyak et al. | 514/267 |
| 4,585,772 | 4/1986 | Junge et al. | 514/267 |
| 4,713,383 | 12/1987 | Francis et al. | 514/267 |
| 4,902,686 | 2/1990 | Wätjen et al. | 514/267 |

FOREIGN PATENT DOCUMENTS 0053767 6/1982 European Pat. Off. .

OTHER PUBLICATIONS

Yoneda et al Chemical Abstracts, vol. 77, No. 126572 1972, p. 896.
Hardtmann et al Journal of Medicinal Chemistry, vol. 18, No. 5, May 1975, pp. 447–453.
Breukink et al Rec. Trav. Chim. 79, 443–453 (1960).
Wegmann et al Helvetica Chimica Acta 29, 1247–1250 (1946).

Primary Examiner—Mukund J. Shah
Assistant Examiner—E. Bernhardt
Attorney, Agent, or Firm—Gordon W. Hueschen

[57] ABSTRACT

New imidazo [1,2-c] quinazoline compounds useful as coronary smooth muscle relaxants and corresponding to the formula:

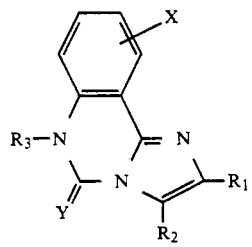

in which:
Y is oxygen or sulfur;
$R_1$ is ($C_1$–$C_6$) alkyl optionally substituted by a phenyl itself optionally substituted, a ($C_3$–$C_6$) cycloalkyl, optionally substituted phenyl, furyl, thienyl or acyl;
$R_2$ is hydrogen, a halogen or a ($C_1$–$C_6$) alkyl optionally substituted by amino or dialkylamino;
$R_3$ is hydrogen, ($C_1$–$C_6$) alkyl optionally substituted by an aryl, or R—CO—($CH_2$)$_n$— [n being 1, 2 or 3, and R being ($C_1$–$C_6$) alkoxy, amino, (alkyl or dialkyl)amino, morpholino or methylpiperazinyl]; and
X is hydrogen or a halogen.

These compounds and their physiologically tolerated salts can be used in medical treatment of coronary smooth-muscle dysfunctions.

10 Claims, No Drawings

IMIDAZO [1,2-C] QUINAZOLINE COMPOUNDS

The subject of the present invention is new imidazo [1,2-c] quinazoline compounds.

In particular it concerns imidazo [1,2-c] quinazoline compounds of general formula I:

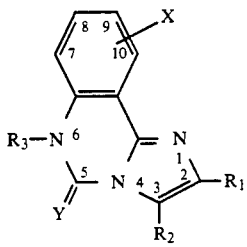

in which:
Y represents an atom of oxygen or of sulfur;
$R_1$ represents:
a) a straight- or branched-chain alkyl radical having 1 to 6 carbon atoms, optionally substituted by a phenyl radical itself optionally mono- or disubstituted by a halogen atom or an alkyl or alkoxy radical each having 1 to 6 carbon atoms in straight- or branched-chain;
b) a mono-, bi- or tricyclic cycloalkyl radical containing 3 to 10 carbon atoms;
c) an aromatic group chosen from among the group formed of:
an unsubstituted phenyl radical and phenyl radicals mono- or disubstituted by a substituent chosen from among halogen atoms and alkyl and alkoxy radicals each having 1 to 6 carbon atoms in straight- or branched-chain, and
a furyl radical and a thienyl radical, or
d) an acyl radical, such as, for example, an alkoxycarbonyl, aminocarbonyl or N,N-dialkylaminocarbonyl radical, in which the alkyl group contains 1 to 6 carbon atoms in straight- or branched-chain, or a benzoyl radical optionally mono- or disubstituted by a halogen atom or an alkyl or alkoxy radical each having 1 to 6 carbon atoms in straight- or branched-chain;

$R_2$ represents a hydrogen or halogen atom or an alkyl radical containing 1 to 6 carbon atoms optionally substituted by an amino, alkylamino or dialkylamino radical in which the alkyl part contains 1 to 6 carbon atoms in straight- or branched-chain;

$R_3$ represents:
a) a hydrogen atom,
b) an alkyl radical having 1 to 6 carbon atoms in straight- or branched-chain, optionally substituted by an aryl radical such as, for example, a phenyl radical itself optionally mono- or polysubstituted by an alkyl or alkoxy radical each having 1 to 6 carbon atoms in straight- or branched-chain, or,
c) a radical of formula:

R—CO—A— in which:
A is a straight- or branched-chain alkylene radical having 1 to 6 carbon atoms, and
R is an alkoxy radical having 1 to 6 carbon atoms or an amino radical of formula:

in which R' and R", identical or different, each represent a hydrogen atom or an alkyl radical containing 1 to 6 carbon atoms in straight- or branched-chain optionally substituted by a hydroxyl radical or alkoxy radical having 1 to 6 carbon atoms, or R' and R" form, together with the nitrogen atom to which they are attached, a pentagonal or hexagonal heterocyclic radical optionally containing a second hetero atom and optionally substituted, such as, for example, a morpholino or N-methylpiperazinyl radical, d) an aryl radical such as, for example, phenyl radical, optionally substituted by one or more alkyl or alkoxy radicals each having 1 to 6 carbon atoms in straight- or branched-chain;

X represents a hydrogen or halogen atom.

The prior art is illustrated in particular by:
Chemical Abstracts 77, 126 572 w, which describes, among others, the compound of imidazo[1,2-c]quinazolin-one of formula:

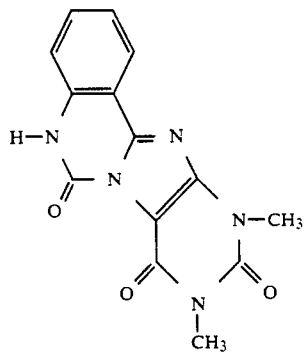

European Patent Application EP 53,767, which describes 2,3-dihydroimidazo[1,2-c]quinazolin-5-ones whose basic formula is:

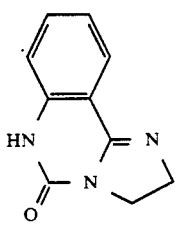

which are useful in the treatment of circulatory diseases,
and Journal of Medicinal Chemistry vol. 18 no. 5, pp. 447-453 (1975) which describes compounds of 10H-imidazo[2,1-b]quinazolin-5-one, and particularly the compound of formula:

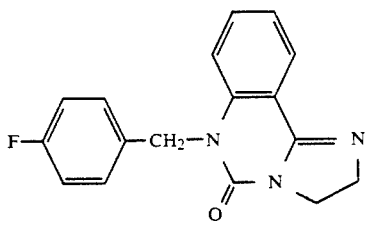

having a bronchodilatory activity.

None of these references describes or suggests the subject of the present invention, that is to say compounds of general formula I, having the pharmacological profile described below.

The subject of the present invention is also a process for preparing compounds of general formula I which comprises,
a compound of general formula II:

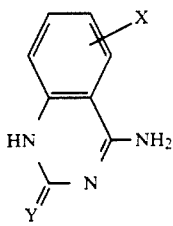
(II)

in which X and Y have the meanings defined above, being acted upon by a halogen compounds of general formula III:

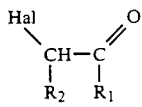
(III)

in which $R_1$ and $R_2$ have the meanings defined above and Hal represents a halogen atom such as, for example, an atom of bromine or chlorine, to obtain the compound of general formula Ia:

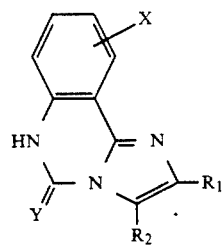
(Ia)

in which X, Y, $R_1$ and $R_2$ have the meanings defined above;
and the compound Ia thus obtained is treated with a base, such as sodium hydride, and then with an alkylating agent of general formula IV:

 (IV)

in which:
$R'_3$ represents:
  a) an alkyl radical having 1 to 5 carbon atoms in straight- or branched-chain, optionally substituted by an aryl radical such as, for example, a phenyl radical itself optionally mono- or polysubstituted by an alkyl or alkoxy radical each having 1 to 5 carbon atoms in straight- or branched-chain, or
  b) a radical of formula:

in which R and A have the meanings defined above; and Hal represents a halogen atom, to obtain the compound of general formula Ib:

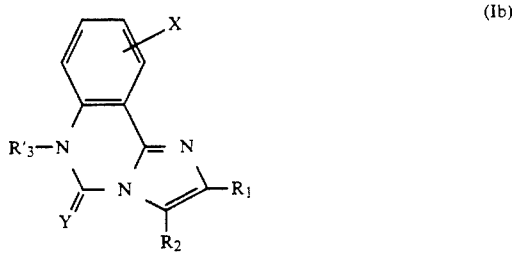
(Ib)

in which X, Y, $R_1$, $R_2$ and $R'_3$ have the meanings defined above.

The process described above can be particularly suitably carried out by performing the reaction of the compounds II and III in a solvent such as, for example, dimethylformamide at a temperature between 25° and 120° C., which enables compounds Ia to be prepared in yields varying from 60 to 85%.

Compounds Ib are beneficially prepared by treating compound Ia with sodium hydride for 30 minutes at room temperature under an inert atmosphere in an aprotic dipolar solvent such as, for example, dimethylformamide.

Compounds of general formula Ia and Ib together form all the compounds of general formula I.

Starting materials of general formula II were prepared starting from anthranilonitrile, according to the process described in Rec. Trav. Chim. Pays-Bas 79, 443 (1960).

The starting materials of general formula III were obtained starting from the corresponding methyl ketones (which are commercially available) by halogenation in ether in the presence of an equivalent amount of halogen, at a temperature varying between 0° and 25° C. for a time between 30 and 120 minutes, depending on the nature of the starting ketone.

The α-bromomethyl ketone thus prepared, which corresponds to formula III, is used as such after washing the ether phase with a sodium bicarbonate solution, drying and evaporating the organic phase. When $R_1$ represents a 3,4-dimethoxyphenyl radical and $R_2$ a hydrogen atom, 3,4-dimethoxyphenacyl bromide precipitates in the reaction medium.

When $R_1$ represents a benzoyl radical and $R_2$ an atom of hydrogen, 3-bromo-1-phenyl-1,2-propanedione is prepared according to the process described in Helvetica Chimica Acta 29, 1247 (1946).

On the other hand, compounds of general formula Ib in which $R'_3$ represents a radical of formula R—CO—A—, in which R is an alkoxy radical having 1 to 6 carbon atoms and A a straight- or branched-chain alkylene radical having 1 to 6 carbon atoms, can be hydrolyzed in an HHal/CH$_3$COOH medium to give the corresponding acids of general formula V:

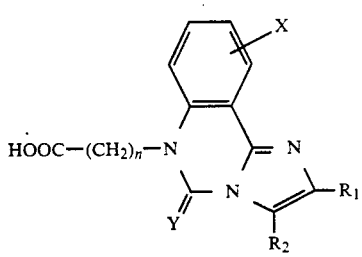

in which X, Y, R₁, R₂ and A have the meanings defined above,
which acids, treated with oxalyl chloride in tetrahydrofuran at 50°-60° C., give the corresponding acyl chlorides which, without a purification step, are treated with an amine of formula:

in which R' and R" have the meanings defined above, to give the compounds of general formula Ic:

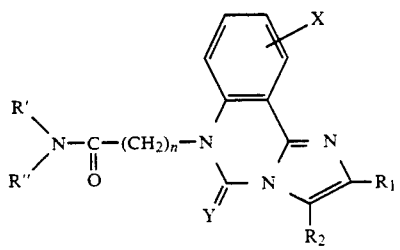

in which X, Y, R₁, R₂, A, R' and R" have the meanings defined above.
which compounds (Ic) are also included in general formula I.

The process for preparing the compounds (Ic) described above, is also included in the present invention.

The compounds of general formula I give salts with physiologically tolerated acids—salts which as such are included in the present invention.

The compounds of general formula I and their physiologically tolerated salts possess valuable pharmacological and therapeutic properties.

In particular, they are selective and specific ligands for peripheral-benzodiazepine receptors. Moreover, these compounds induce relaxation in the smooth muscle fibers situated in the blood vessels, kidneys, the bronchi, etc.

Consequently, the compounds of the present invention prove to be useful for treating acute anginal crisis, the prophylactic treatment of angina pectoris crisis and ischemia, the treatment of hypertension, of arteriosclerosis and of other hyperproliferative ailments, and the treatment of asthma. They are also useful in the treatment of anxiety, depression and immunological disorders.

The subject of the present invention is also pharmaceutical compositions containing as active principle a compound of general formula I or one of its physiologically tolerated salts, mixed or associated with an appropriate pharmaceutical excipient such as, for example, glucose, lactose, starch, talc, ethylcellulose, magnesium stearate or cocoa butter.

The pharmaceutical compositions thus obtained are generally in the form of measured doses, and can contain from 1 to 10 mg of active principle. They can take the form, for example, of tablets, pills, capsules, suppositories, injectable or orally administered solutions, and can, as appropriate, be administered orally, rectally or parenterally at a dosage of 1 to 10 mg one to two times per day.

The following examples illustrate the present invention.

EXAMPLE 1

2-Ethoxycarbonyl-5-oxo-5,6-dihydroimidazo[1,2-c]quinazoline

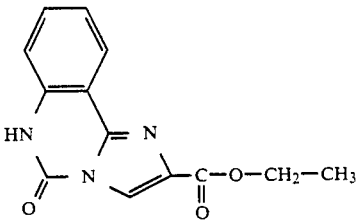

1.65 ml (0.013 mol) of ethyl bromopyruvate are added to 1.5 g (0.009 mol) of 4-amino-2-quinazolinone in 40 ml of dimethylformamide. After stirring for 15 hours at room temperature, sodium acetate is added until a pH of 5 is obtained. Stirring is continued for 36 hours adjusting the pH to 5, then water is added and the solution is filtered.

The solid portion (910 mg) is dried, then put into 40 ml of ethanol in the presence of a catalyst, p-toluenesulfonic acid. The reaction medium is refluxed for 2 hours, then cooled and filtered to separate the white crystals thus formed.

The mother liquor is extracted with ethyl acetate. After drying over MgSO₄, and evaporating to dryness in a rotary evaporator, the residue is heated under reflux in ethanol in the presence of p-toluenesulfonic acid as before, then the mixture is left to cool and the crystals obtained are filtered out.

After recrystallization in ethanol at 95° C., 2-ethoxycarbonyl-5-oxo-5,6-dihydroimidazo[1,2-c]quinazoline is obtained in the form of white crystals which melt at 264°-266° C.

Yield: 58%.

TLC (CH₃COOC₂H₅/hexane; 1:1): $R_f = 0.33$

NMR (TFA): $\delta = 1.5$ (t, 3H, J=7 Hz); 4.7 (g, 2H, J=7 Hz); 7.6–8.2 (m, 3H); 8.4–8.7 (m, 1H); 8.8 (s, 1 H).

EXAMPLE 2

2-Ethoxycarbonyl-6-N,N-diethylaminocarbonylmethyl-5-oxo-5,6-dihydroimidazo[1,2-c]quinazoline

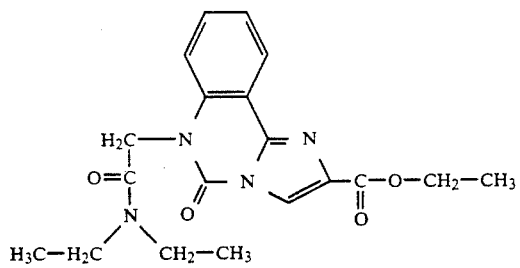

0.038 g (1.1 equivalents) of sodium hydride is added to 0.2 g (0.007 mol) of 2-ethoxycarbonyl-5-oxo-5,6-dihydroimidazo[1,2-c]quinazoline dissolved in 4 ml of dimethylformamide and stirring is continued for 30 minutes under an atmosphere of argon. 0.21 ml (0.001 mol) of chloro-N,N-diethylacetamide is added. The stirring is continued for 15 hours, then 30 ml of water are added and the precipitate obtained is filtered out.

After chromatography on a silica column eluting with $CH_3COOC_2H_5$ 2-ethoxycarbonyl-6-N,N-diethylaminocarbonylmethyl-5-oxo-5,6-dihydroimidazo[1,2-c]quinazoline, melting at 170° C., is gathered.

Yield: 50%.

TLC ($CH_3COOC_2H_5$): $R_f$: 0.5

NMR ($CDCl_3$): $\delta = 1.16$ (m, 9H); 3.2–3.6 (m. 4H); 4.4 (g, 2H, J=7 Hz); 6.2 (s, 1H); 7–7.7 (m, 3H); 8.4 (s, 1H); 8.4–8.6 (m, 1H).

EXAMPLE 3

2-Phenyl-5-oxo-5,6-dihydroimidazo[1,2-c]quinazoline

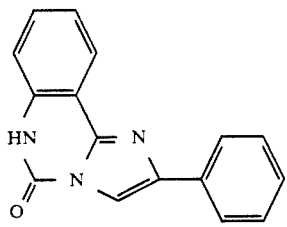

1.61 g (0.01 mol) of 4-amino-2-quinazolinone and then 2.2 g (0.011 mol) of phenacyl bromide are added to 25 ml of dimethylformamide. The mixture is heated at 120° C. (external heating) for 3 hours, then left to cool and water is added. The brown precipitate formed is filtered out (1.34 g).

Yield: 52%.

The product thus obtained is sufficiently pure to be used as such for the syntheses which follow.

A sample was purified by chromatography on a silica column, eluted with $CH_3COOC_2H_5$/hexane (1:1), pure 2-phenyl-5-oxo-5,6-dihydroimidazo[1,2-c]quinazoline is obtained, m.p.: 278°–280° C.

TLC ($CH_3COOC_2H_5$/hexane 1:1): $R_f$: 0.65

NMR (DMSO): $\delta = 3.3$ (s broad, 1H); 7.1–7.7 (m, 6H); 7.9–8.3 (m, 3H); 8.4 (s, 1H).

The starting 4-amino-2-quinazolinone was prepared according to the process of K. W. BREUKINK and P. E. VERKADE—Rec. Trav. Chim. 79, 443–453 (1960).

EXAMPLE 4

2-Aminocarbonyl-6-N,N-diethylaminocarbonylmethyl-5-oxo-5,6-dihydroimidazo[1,2-c]quinazoline

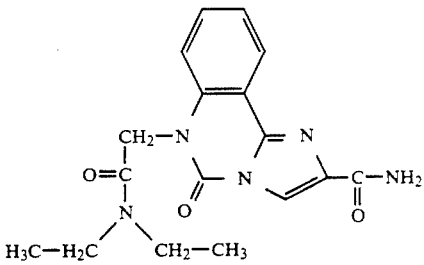

0.3 g (0.0008 mol) of 2-ethoxycarbonyl-6-N,N-diethylaminocarbonylmethyl-5-oxo-5,6-dihydroimidazo[1,2-c]quinazoline is added to 25 ml of methanol. The solution is saturated and cooled in an ice bath with ammonia. It is stirred for 17 hours at room temperature; then a third of the solution is evaporated in a rotary evaporator and the precipitate formed is filtered out.

The solid is crystallized in methanol and 0.14 g of 2-aminocarbonyl-6-N,N-diethylaminocarbonylmethyl-5-oxo-5,6-dihydroimidazo[1,2-c]quinazoline, melting at 248°–249° C., is obtained.

Yield: 52%.

TLC ($CH_3COOC_2H_5$): $R_f = 0.2$

NMR (DMSO): $\delta = 1.10$ (t, 3H, $\delta = 8$ Hz); 1.35 (t, 3H, $\delta = 8$ Hz); 3.38 (g, 2H, 8 Hz); 3.58 (g, 2H, $\delta = 8$ Hz); 5.28 (s, 2H); 7.40–7.50 (m, 2H); 7.63 (s, 1H); 7.69–7.73 (m, 1H); 7.67 (s, 1H); 8.30 (s, 1H); 8.32–8.36 (m, 1H).

EXAMPLE 5

2-Phenyl-3-dimethylaminomethyl-6-N,N-diethylaminocarbonylmethyl-5-oxo-5,6-dihydroimidazo[1,2-c]quinazoline

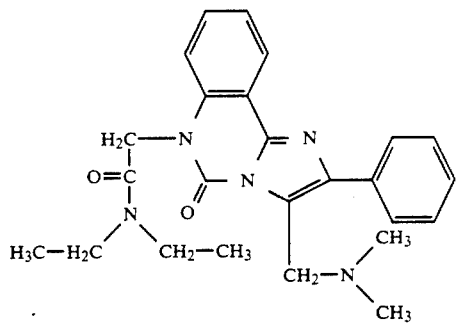

a) 0.56 g of glacial acetic acid is added to 0.55 g of a 35% solution of dimethylamine cooled to 5° C., then 0.40 g of a 35% solution of formol (also cooled) is added at this same temperature.

The mixture is stirred gently and poured into a round bottom flask containing 1.04 g ($4.10^{-3}$ mol) of 2-phenyl-5-oxo-5,6-dihydroimidazo[1,2-c]quinazoline.

The mixture is heated until the product dissolves (about 90° C.) and then left at room temperature for 24 hours.

1N sodium hydroxide is added until the pH is 8 and the product is extracted with ethyl acetate, washed with water, dried over $Na_2SO_4$ and evaporated to dryness.

The product is purified by passage on a silica column, eluting with ethyl acetate containing 5% of triethylamine. 0.74 g (2.3.10$^{-3}$ mol) of 2-phenyl-3-dimethylaminomethyl-5-oxo-5,6-dihydroimidazo[1,2-c]quinazoline is thus recovered, in the form of a white powder melting at 189°–191° C.

Yield: 50%.

TLC [CH$_3$COOC$_2$H$_5$ with 5% of N(C$_2$H$_5$)$_3$]: R$_f$=0.3
NMR (CDCl$_3$): 8.4–7.2: m, 9H, aromatic;

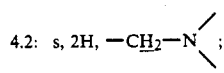
4.2: s, 2H, —CH$_2$—N$\backslash$

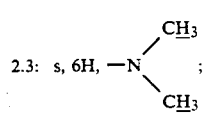
2.3: s, 6H, —N(CH$_3$)$_2$;

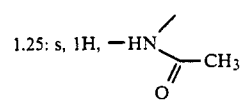
1.25: s, 1H, —HN—C(=O)—CH$_3$ b) 0.35 g (1.1.10$^{-3}$ mol) of 2-phenyl-3-dimethylaminomethyl-5-oxo-5,6-dihydroimidazo[1,2-c]quinazoline is dissolved in 10 ml of dimethylformamide in a well-dried 50 ml round bottom flask.

0.03 g (1.21.10$^{-3}$ mol) of sodium hydride is added and the mixture is left under agitation for half an hour. A uniform yellow solution is thus obtained.

0.3 ml (2.2.10$^{-3}$ mol) of 2-chloro-N,N-diethylacetamide is added, and the agitation is continued overnight at room temperature. Water is then added slowly to the reaction medium which is then left overnight. The precipitate formed is filtered out and the aqueous phase is extracted with CH$_2$Cl$_2$, dried over Na$_2$SO$_4$ and evaporated to dryness.

The two precipitates are gathered together and dried by a vane pump. The product is purified by passage through a silica column, eluting with the system CH$_3$COOC$_2$H$_5$/N(CH$_3$)$_3$ (95:5). 0.19 g (0.44.10$^{-3}$ mol) of 2-phenyl-3-dimethylaminomethyl-6-N,N-diethylaminocarbonylmethyl-5-oxo-5,6-dihydroimidazo[1,2-c]quinazoline are recovered, in the form of a white powder melting at 192°–194° C.

Yield: 40%.

| | Microanalysis: | | |
|---|---|---|---|
| | C % | H % | N % |
| Calculated: | 69.58 | 6.77 | 16.23 |
| Found: | 69.44 | 6.91 | 15.90 |

TLC (CH$_3$COOC$_2$H$_5$-N(C$_2$H$_5$)$_3$; 95:5): R$_f$=0.54
NMR (200 MHz) (CDCl$_3$): 9.49–6.99: m, 9H, aromatic;

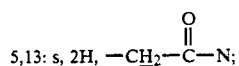
5,13: s, 2H, —CH$_2$—C(=O)—N;

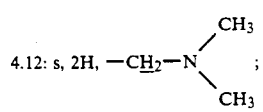
4.12: s, 2H, —CH$_2$—N(CH$_3$)$_2$;

-continued 3.56–3.41: s, 4H, 2 × —CH$_2$—CH$_3$;

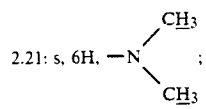
2.21: s, 6H, —N(CH$_3$)$_2$;

1.40: t, J=7, 3H, —CH$_2$—CH$_3$;

1.18: t, J=7.06, 3H, —CH$_2$—CH$_3$

EXAMPLE 6

2-Benzoyl-6-N,N-diethylaminocarbonylmethyl-5-oxo-5,6-dihydroimidazo[1,2-c]quinazoline

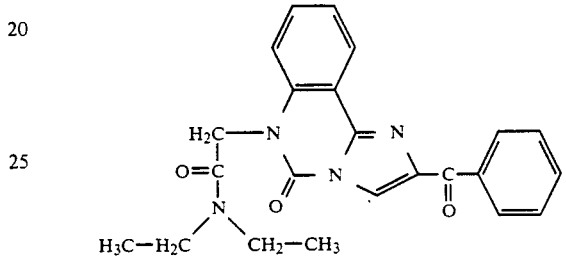

a) 1 g (6.2.10$^{-3}$ mol) of 4-amino-2-quinazolinone in 10 ml of dimethylformamide, and 1.55 g (6.8.10$^{-3}$ mol) of 3-bromo-1-phenyl-1,2-propanedione are added to a 50 ml round bottom flask.

After stirring for 15 hours at room temperature a uniform orange solution is obtained. Cold water is gently added to this and then it is cooled in an ice bath. The precipitate formed is filtered out, dried and washed in ether.

The product is purified by recrystallization in ethanol 0 65 g (2.25.10$^{-3}$ mol) of 2-benzoyl-5-oxo-5,6-dihydroimidazo[1,2-c]quinazoline is recovered, in the form of yellow crystals melting at 260° C.

Yield: 36%.

TLC (CH$_3$COOC$_2$H$_5$): R$_f$=0.8

NMR (DMSO): 8.3: s, 1H, imidazole-H; 8.0–8.2: m, 3H, aromatic; 7.1–7.8: m, 6H, aromatic; 3.5: s broad, 1H, HN< b) 0.53 g (1.82.10$^{-3}$ mol) of 2-benzoyl-5-oxo-5,6-dihydroimidazo[1,2-c]quinazoline is dissolved in 10 ml of dimethylformamide in a well-dried 50 ml round bottom flask.

0.05 g (2.10$^{-3}$ mol) of sodium hydride is added. Stirring is continued at room temperature for half an hour, and a uniform black solution is thus obtained To this is added 0.60 ml (3.7.10$^{-3}$ mol) of 2-chlorodiethylacetamide, and stirring is continued overnight at room temperature. Water is added slowly to the reaction mixture. The mixture is filtered using a water pump and the product is dried using a vane pump.

After recrystallization in methanol, 0.47 g (1.2.10$^{-3}$ mol) of 2-benzoyl-6-N,N-diethylaminocarbonylmethyl-5-oxo-5,6-dihydroimidazo[1,2-c]quinazoline is recovered, in the form of pale yellow crystals melting at 217°–218° C.

Yield: 65%.

| Microanalysis: | | | |
|---|---|---|---|
| | C % | H % | N % |
| Calculated: | 68.64 | 5.51 | 13.92 |
| Found: | 68.76 | 5.44 | 14.19 |

TLC (CH₃COOC₂H₅/hexane; 1:1): $R_f$=0.35
NMR (200 MHz) (CDCl₃): 8.57–7.07: m, 9H, aromatic; 8.37: s, 1H, imidazo-H; 5.14: s, 2H,

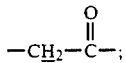

3.58–3.41: m, 4H, 2 X -C$\underline{H}_2$-CH₃; 1.41 t, J=7.12, 3H, -CH₂-C$\underline{H}_3$; 1.18: t, J=7.15, 3H, -CH₂-C$\underline{H}_3$.

EXAMPLE 7

2-Phenyl-3-bromo-6-N,N-diethylaminocarbonylmethyl-5-oxo-5,6-dihydroimidazo[1,2-c]quinazoline

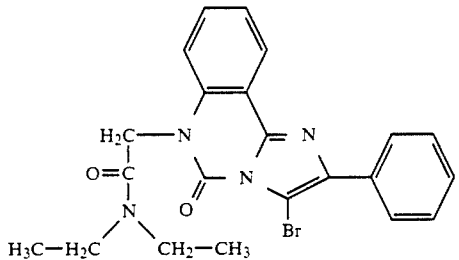

a) An equimolar mixture (2.10$^{-3}$ mol) of 2-phenyl-5-oxo-5,6-dihydroimidazo[1,2-c]quinazoline and N-bromosuccinimide is put to reflux for 16 hours in chloroform.

After verifying the end of the reaction on a silica gel plate, the chloroform is evaporated, and the product is chromatographed on a silica column (eluent: CH₃COOC₂H₅/hexane, 1:1). 0.44 g (1.3.10$^{-3}$ mol) of 2-phenyl-3-bromo-5-oxo-5,6-dihydroimidazo[1,2-c]quinazoline is thus recovered, in the form of a white powder melting at 235°–237° C.

Yield: 65%.

TLC (CH₃COOC₂H₅/hexane; 1:1): $R_f$=0.5
NMR (DMSO): disappearance of the imidazole-H singlet.

b) 2-Phenyl-3-bromo-6-N,N-diethylaminocarbonylmethyl-5-oxo-5,6-dihydroimidazo[1,2-c]quinazoline is synthesized beginning from the 2-phenyl-3-bromo-5-oxo-5,6-dihydroimidazo[1,2-c]quinazoline prepared above and 2-chloro-N,N-diethylacetamide according to the method described in Example 6b).

Yield: 50%.
M.p.: 245°–247° C.

| Microanalysis: | | | |
|---|---|---|---|
| | C % | H % | N % |
| Calculated: | 58.28 | 4.67 | 12.34 |
| Found: | 58.32 | 4.64 | 12.20 |

TLC (CH₃COOC₂H₅/hexane; 1:1): $R_f$=0.4
NMR (CDCl₃): 8.45–6.97: m, 9H, aromatic; 5.03: s, 2H,

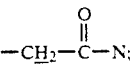

3.43–3.38: m, 4H, 2 X -CH₂-CH₃; 1.36–1.26: m, 3H, -CH₂-C$\underline{H}_3$; 1.16–1.09: m, 3$\overline{H}$, =$\overline{C}$H₂-C$\underline{H}_3$.

EXAMPLES 8–33

By proceeding, according to the meanings of the substituents R₁, R₂ or R₃, as described in the previous examples, the compounds mentioned in the following examples were prepared:

8) 2-ethoxycarbonyl-6-methyl-5-oxo-5,6-dihydroimidazo[1,2-c]quinazoline; m.p.: 215°–216° C.
9) 2-benzoyl-5-oxo-5,6-dihydroimidazo[1,2-c]quinazoline; m.p.: 260° C.
10) 2-ethoxycarbonyl-6-benzyl-5-oxo-5,6-dihydroimidazo[1,2-c]quinazoline; m.p.: 167°–168° C.
11) 2-phenyl-6-N,N-diethylaminocarbonylmethyl-5-oxo-5,6-dihydroimidazo[1,2-c]quinazoline; m.p.: 183°–185° C.
12) 2-phenyl-6-N-methylpiperazinocarbonylmethyl-5-oxo-5,6-dihydroimidazo[1,2-c]quinazoline; m.p.: of the corresponding hydrochloride: 280°–281° C.
13) 2-phenyl-6-ethoxycarbonylmethyl-5-oxo-5,6-dihydroimidazo[1,2-c]quinazoline; m.p.: 229° C.
14) 2-phenyl-6-N-isopropylaminocarbonylmethyl-5-oxo-5,6-dihydroimidazo[1,2-c]quinazoline; m.p.: 274° C.
15) 2-(p-chlorophenyl)-6-N,N-diethylaminocarbonylmethyl-5-oxo-5,6-dihydroimidazo[1,2-c]quinazoline: m.p.: 252° C.
16) 2-phenyl-6-morpholinocarbonylmethyl-5-oxo-5,6-dihydroimidazo[1,2-c]quinazoline; m.p.: 273°–274°C.
17) 2-(p-methoxyphenyl)-6-N,N-diethylaminocarbonylmethyl-5-oxo-5,6-dihydroimidazo[1,2-c]quinazoline; m.p.: 210°–212° C.
18) 2-(p-methylphenyl)-6-N,N-diethylaminocarbonylmethyl-5-oxo-5,6-dihydroimidazo[1,2-c]quinazoline; m.p.: 233°–234° C.
19) 2-(m-chlorophenyl)-6-N,N-diethylaminocarbonylmethyl-5-oxo-5,6-dihydroimidazo[1,2-c]quinazoline; m.p.: 224°–225° C.
20) 2-phenyl-3-methyl-6--N,N-diethylaminocarbonylmethyl-5-oxo-5,6-dihydroimidazo[1,2-c]quinazoline; m.p.: 192° C.
21) 2-(2-furyl)-6-N,N-diethylaminocarbonylmethyl-5-oxo-5,6-dihydroimidazo[1,2-c]quinazoline; m.p.: 194° C.
22) 2-(3-thienyl)-6-N,N-diethylaminocarbonylmethyl-5-oxo-5,6-dihydroimidazo[1,2-c]quinazoline; m.p.: 227° C.
23) 2-(3,4-dimethoxyphenyl)-6-N,N-diethylaminocarbonylmethyl-5-oxo-5,6-dihydroimidazo[1,2-c]quinazoline; m.p.: 204° C.
24) 2-phenyl-6-N-isobutylaminocarbonylmethyl-5-oxo-5,6-dihydroimidazo[1,2-c]quinazoline; m.p.: 285° C.
25) 2-phenyl-3-ethyl-6-N,N-diethylaminocarbonylmethyl-5-oxo-5,6-dihydroimidazo[1,2-c]quinazoline; m.p.: 180°–181° C.
26) 2-phenyl-6-N,N-diethylaminocarbonylpropyl-5-oxo-5,6-dihydroimidazo[1,2-c]quinazoline; m.p.: 149° C.
27) 2-phenyl-6-ethoxycarbonylpropyl-5-oxo-5,6-dihydroimidazo[1,2-c]quinazoline, m.p.: 126° C.

28) 2-phenyl-6-N,N-dipropylaminocarbonylmethyl-5-oxo-5,6-dihydroimidazo[1,2-c]quinazoline; m.p.: 189° C.
29) 2-phenyl-6-methyl-5-oxo-5,6-dihydroimidazo[1,2-c]quinazoline; m.p.: 222°–225° C.
30) 2-(o-chlorophenyl)-6-N,N-diethylaminocarbonylmethyl-5-oxo-5,6-dihydroimidazo[1,2-c]quinazoline; m.p.: 188° C.
31) 2-phenyl-6-N,N-diethylaminocarbonylmethyl-10-chloro-5-oxo-5,6-dihydroimidazo[1,2-c]quinazoline; m.p.: 219°–220° C.
32) 2-(m-chlorophenyl)-3-methyl-6-N,N-dipropylaminocarbonylmethyl-5-oxo-5,6-dihydroimidazo[1,2-c]quinazoline; m.p.: 199°–201° C.
33) 2-(tert-butyl)-6-N,N-diethylaminocarbonylmethyl-5-oxo-5,6-dihydroimidazo[1,2-c]quinazoline; m.p.: 179° C.
34) 2-adamantanyl-6-N,N-diethylacetamido-5-oxo-5,6-dihydroimidazo[1,2-c]quinazoline; m.p.: 260°–261° C.
35) 2-phenyl-6-benzoylmethyl-5-oxo-5,6-dihydroimidazo[1,2-c]quinazoline; m.p.: 273°–275° C.
36) 2-(3,4-dimethoxyphenyl)-6-benzyl-5-oxo-5,6-dihydroimidazo[1,2-c]quinazoline; m.p.: 210°–212° C.
37) 2-phenyl-6-piperidinocarbonylmethyl-5-oxo-5,6-dihydroimidazo[1,2-c]quinazoline; m.p.: 245°–246° C.
38) 2-phenyl-6-N-phenylacetamido-5-oxo-5,6-dihydroimidazo[1,2-c]quinazoline; m.p.: 292°–294° C.
39) 2-phenyl-6-(N-methyl-N-phenylacetamido)-5-oxo-5,6-dihydroimidazo[1,2-c]quinazoline; m.p.: 240°–242° C.
40) 2-(tert-butyl)-6-N-N-dipropylacetamido-5-oxo-5,6-dihydroimidazo[1,2-c]quinazoline; m.p.: 145°–146° C.
41) 2-(m-chlorophenyl)-6-(N-methyl-N-phenylacetamido)-5-oxo-5,6-dihydroimidazo[1,2-c]quinazoline; m.p.: 237°–238° C.
42) 2-(m-chlorophenyl)-3-bromo-6-(N-methyl-N-phenylacetamido)-5-oxo-5,6-dihydroimidazo[1,2-c]quinazoline; m.p.: 245°–247° C.
43) 2-phenyl-6-(N,N-diethylmethylacetamido)-5-oxo-5,6-dihydroimidazo[1,2-c]quinazoline; m.p.: 170° C.
44) 2-phenyl-6-(N,N-di(2-methoxyethyl)acetamido)-5-oxo-5,6-dihydroimidazo[1,2-c]quinazoline; m.p.: 203°–204° C.

EXAMPLE 4

Pharmacological Study

The action of the compounds of the present invention has been demonstrated from results of biochemical and physiological experiments. The specificity of action as well as the selectivity of the compounds studied with regard to so-called peripheral receptors for benzodiazepines have been demonstrated. The combination of the compounds studied with their receptor has been shown to have no notable pharmacological effect on the heart and the central nervous system and to be highly selective for coronary smooth muscle. The compounds studied induce a dose-dependent relaxation in smooth muscle precontracted by addition of PGF$_{2\alpha}$. The relaxation induced by the compounds of the present invention was evaluated in comparison with some reference products: efloxate, dipyridamole, RO5-4864, PK 11195 and diazepam.

A) Materials and methods

All the products studied were dissolved in DMSO at a concentration of $10^{-2}$M, then diluted to the desired concentrations in the experimental media. All of the ED$_{20}$, ED$_{50}$ and K$_{0.5}$ values were corrected for the values obtained with DMSO under the same conditions of dilution.

1) Binding studies

Binding studies were carried out on microsomal fractions from the central nervous system of the rat, [KRUEGER B. K., RATZLAFF R. W., STRICHARTZ G. R. and BLAUSTEIN M. P., Saxitoxin binding to synaptosomes, membranes and solubilized binding sites from rat brain, J. Membrane Biol., 50, 287–310 (1979)] for the studies on the displacement of [$^3$H]-RO 151788 fixed specifically to the central receptors for benzodiazepines [MÖHLER H., BURKARD W. P., KELLER H. H., RICHARDS J. G. and HAEFELY W.: Benzodiazepines antagonist RO-151788: binding characteristics and interaction with drug induced changes in dopamine turnover and cerebellar GMP levels. J. Neurochem., 37, 714–722 (1981)], and on microsomal fractions from rat heart [LOMBET A., RENAUD J. F., CHICHEPORTICHE R. and LAZDUNSKI M.: A cardiac tetrodotoxin binding component: biochemical identification, characterization and properties. Biochemistry, 20, 1279–1285 (1981)] for the studies on the displacement of [$^3$H]-PK 11195 and of RO5-4864 fixed specifically to the so-called peripheral receptors for benzodiazepines [LE FUR G., VAUCHER N., PERRIER M. L., FLAMIER A., BENAVIDES J., RENAULT C., DUBROEUCQ M. C., GUEREMY C. and UZAN A.: Differentiation between two ligands for peripheral benzodiazepine binding site [$^3$H]-RO5-4864 and [$^3$H]-PK 11195 by thermodynamic studies. Life Sci., 33, 449–457, (1983)]. The experiments on the displacement of different radio-labeled ligands by the reference molecules and the compounds of the present invention were each conducted under the standard conditions of binding mentioned above. In every case, after the time required for combination, the bound radioactivity was separated from the free component by filtration under vacuum on filter GF/C. The radioactivity remaining on the filters is then determined by counting in liquid scintillation.

2) Ionic fluxes

Influxes of Na$^+$ via the Na$^+$ channel, the function of which is dependent on membrane potential, via Na$^+$/H$^+$ exchange, Na$^+$/K$^+$/2Cl$^-$ cotransport and the Na$^+$ pump, were determined according to previously published protocols [FRELIN C., VIGNE P. and LAZDUNSKI M.: The role of the Na$^+$/H$^+$ exchange in the regulation of the internal pH in cultured cardiac cells Eur. J. Biochem., 149, 1–4 (1985)—RENAUD J. F., Internal pH, Na$^+$ and Ca$^{2+}$ regulation by trimetazidine during cardiac cell acidosis. Cardiovasc. Drugs Ther, 1, 677–686 (1988)—FRELIN C., CHASSANDE O. and LAZDUNSKI M.: Biochemical characterization of the Na$^+$/K$^+$/2Cl$^-$ co-transport in chick cardiac cells. Biochem. Biophys. Res. Commun., 134, 326–331 (1986) and KAZAZOGLOU T., RENAUD J. F., ROSSI B. and LAZDUNSKI M.: Two classes of ouabain receptors in chick ventricular cardiac cells and their relation to (Na$^+$, K$^+$) ATPase inhibition, intracellular Na$^+$ accumulation, Ca$^{2+}$ influx and cardiotonic effect. J. Biol. Chem., 258, 12163–12170 (1983)] using cardiac cells. The influxes of Ca$^{2+}$ via the slow Ca$^{2+}$ channel and via Na$^+$/Ca$^{2+}$ exchange were determined using a line of A$_{7r5}$ aortic cells from rats [GALIZZI J. P., QAR J., FOSSET M., VAN RENTERGHEM C.

and LAZDUNSKI M.: Regulation of calcium channels in aortic muscle cells by protein kinase C activators (diacylglycerol and phorbol esters) and by peptides (vasopressin and bombesin) that stimulate phosphoinositide breakdown. J. Biol. Chem., 262, 6947–6950 (1987)], and cardiac cells [KAZAZOGLOU T., RENAUD J. F., ROSSI B. and LAZDUNSKI M.: Two classes of ouabain receptors in chick ventricular cardiac cells and their relation to (Na+, K+) ATPase inhibition, intracellular Na+ accumulation, $Ca^{2+}$ influx and cardiotonic effect. J. Biol. Chem., 258, 12163–12170 (1983)], respectively.

3) Porcine coronary relaxation

Coronaries were taken on the heart of pigs (Yucatan mini pig), anesthetized under stresnil and pentobarbital. Proximal segments of the coronary were placed in an organ tank filled with Ringer solution at 37° C. The segments were tightened progressively to a base tension of around 6 g and contracted by the addition of $PGF_{2\alpha}$ at a concentration of $4.10^{-6}M$. The potential of the products of the present invention to relax the coronary artery were then tested.

B) Results 1) Binding studies

This work was carried out by displacing RO 151788 fixed specifically on the central benzodiazepine receptors (rat central nervous system), as well as by displacing PK 11195 and RO5-4864 fixed specifically on the peripheral benzodiazepine receptors from rat heart. These studies enabled us to pick out compounds exhibiting an excellent selectivity for the peripheral receptors with affinities between $10^{-7}M$ and $10^{-8}M$ (Table I). Good correlation was found between the values obtained for the displacement by the compounds of the present invention of the agonist and of the antagonist fixed specifically to the peripheral receptor site. Moreover these compounds were tested for possible interactions with receptors for adenosine ($A_1$, $A_2$), alpha-($\alpha_1$, $\alpha_2$) and beta-adrenergic receptors, dopamine ($D_1$, $D_2$) receptors, serotonin ($5HT_{1A}$, $5HT_{1B}$, $5HT_2$) receptors and GABA receptors. No significant interaction could be shown for any of the compounds examined.

2) Ion flux and ion transport

These studies were carried out on cardiac cells and smooth muscle cells in in vitro culture conditions. All compounds were shown to be inactive on the systems tested: Na+ channel; $Ca^{2+}$ channel; Na+/H+ exchange; Na+/$Ca^{2+}$ exchange; Na+/K+/2Cl− cotransport and the Na+ pump.

3) Porcine coronary relaxation

All of the compounds were tested for their capacity to relax the porcine coronary precontracted by $PGF_{2\alpha}$. The results obtained (Table II) show that there exists a good correlation between the level of relaxation obtained ($ED_{50}$) and the values for 50% effect ($K_{0.5}$) obtained after displacement of [$^3H$]-PK 11195 and of [$^3H$]-RO5-4864 fixed specifically to the peripheral receptor.

The level of relaxation obtained as well as the 50% effect value ($K_{0.5}$) obtained by displacement show that the compounds of Examples 10, 11, 17, 28 and 32 are particularly favorable.

TABLE I

Specificity of action of compounds of the invention vis-a-vis peripheral receptors labeled with PK 11195 and RO5-4864 and central receptors labeled with RO 151788

| Products tested | Peripheral receptors [$^3H$]—PK 11195 $K_{0.5}$ (M) | [$^3H$]—RO 54864 $K_{0.5}$ (M) | Central receptors [$^3H$]—RO 151788 $K_{0.5}$ (M) |
|---|---|---|---|
| Example 1 | $>10^{-4}$ | $6.1\ 10^{-5}$ | $10^{-6}$ |
| Example 2 | $5.5\ 10^{-7}$ | / | $7\ 10^{-5}$ |
| Example 3 | $4.5\ 10^{-6}$ | $>>10^{-4}$ | $3.5\ 10^{-7}$ |
| Example 4 | $8\ 10^{-6}$ | $6\ 10^{-6}$ | $>10^{-4}$ |
| Example 5 | $2.2\ 10^{-6}$ | $4.5\ 10^{-6}$ | $1.8\ 10^{-4}$ |
| Example 6 | $2.2\ 10^{-7}$ | $2\ 10^{-7}$ | $4.6\ 10^{-5}$ |
| Example 8 | $>>10^{-4}$ | $3\ 10^{-5}$ | $1.3\ 10^{-4}$ |
| Example 9 | $2.8\ 10^{-5}$ | $1.3\ 10^{-5}$ | $1.5\ 10^{-7}$ |
| Example 10 | $\sim 10^{-4}$ | $8.8\ 10^{-6}$ | $4\ 10^{-6}$ |
| Example 11 | $4\ 10^{-7}$ | $8\ 10^{-8}$ | $>10^{-4}$ |
| Example 12 | $8\ 10^{-5}$ | $4\ 10^{-5}$ | $>>10^{-4}$ |
| Example 13 | $10^{-4}$ | $>>10^{-4}$ | $>10^{-4}$ |
| Example 14 | $>>10^{-4}$ | $>>10^{-4}$ | $>10^{-4}$ |
| Example 15 | $1.5\ 10^{-6}$ | $\sim 10^{-4}$ | $>10^{-4}$ |
| Example 16 | $>10^{-4}$ | $>10^{-4}$ | $>10^{-4}$ |
| Example 17 | $1.4\ 10^{-7}$ | $1.2\ 10^{-7}$ | $10^{-4}$ |
| Example 18 | $2.1\ 10^{-7}$ | $7\ 10^{-8}$ | $10^{-4}$ |
| Example 19 | $5.8\ 10^{-8}$ | $5\ 10^{-8}$ | $>10^{-4}$ |
| Example 20 | $2.9\ 10^{-8}$ | $8.6\ 10^{-9}$ | $6\ 10^{-5}$ |
| Example 21 | $2.6\ 10^{-7}$ | $5.8\ 10^{-7}$ | $>10^{-4}$ |
| Example 22 | $2\ 10^{-7}$ | $1.3\ 10^{-7}$ | $>10^{-4}$ |
| Example 23 | $1.5\ 10^{-7}$ | $5\ 10^{-7}$ | $>10^{-4}$ |
| Example 24 | $>>10^{-4}$ | $>>10^{-4}$ | $>10^{-4}$ |
| Example 25 | $3.2\ 10^{-8}$ | $5\ 10^{-8}$ | $5\ 10^{-5}$ |
| Example 26 | $10^{-5}$ | $2.3\ 10^{-6}$ | $10^{-4}$ |
| Example 27 | $>>10^{-4}$ | $6\ 10^{-5}$ | $10^{-4}$ |
| Example 28 | $1.1\ 10^{-8}$ | $1.2\ 10^{-8}$ | $10^{-4}$ |
| Example 29 | $>>10^{-4}$ | $>10^{-4}$ | $1.5\ 10^{-4}$ |
| Example 30 | $2.8\ 10^{-7}$ | $3.4\ 10^{-8}$ | $1.2\ 10^{-4}$ |
| Example 31 | $1.4\ 10^{-6}$ | $2.8\ 10^{-6}$ | $10^{-4}$ |
| Example 32 | $2.4\ 10^{-9}$ | $3.1\ 10^{-9}$ | $>10^{-4}$ |
| Reference products | | | |
| Efloxate | $2\ 10^{-5}$ | $2\ 10^{-4}$ | $2\ 10^{-5}$ |
| Dipyridamole | $3\ 10^{-7}$ | $2\ 10^{-7}$ | $2.8\ 10^{-7}$ |
| RO5-4864 | $1\ 10^{-7}$ | $9\ 10^{-11}$ | $6\ 10^{-5}$ |
| PK 11195 | $1\ 10^{-9}$ | $2\ 10^{-10}$ | $1.5\ 10^{-5}$ |
| Diazepam | $4\ 10^{-7}$ | $2\ 10^{-7}$ | $2.7\ 10^{-9}$ |

TABLE II

Effect of the compounds of the invention on coronary tension induced by $PFG_{2\alpha}$

| Products tested | Number of experiments | $DE_{20}$ (M) | $DE_{50}$ (M) | Confidence interval [$10^{-6}M$] |
|---|---|---|---|---|
| Example 1 | 4 | | | No effect |
| Example 2 | 0 | | | |
| Example 3 | 5 | $3.54\ 10^{-5}$ | $7.48\ 10^{-6}$ | |
| Example 4 | 5 | $5.74\ 10^{-5}$ | $9.66\ 10^{-6}$ | |
| Example 5 | 5 | $1.44\ 10^{-4}$ | $1.89\ 10^{-5}$ | $0.83 < DE_{50} < 431.9$ |
| Example 8 | 4 | | | No effect |
| Example 9 | 4 | | | No effect |
| Example 10 | 7 | $3.33\ 10^{-6}$ | $1.04\ 10^{-6}$ | $0.39 < DE_{50} < 2.79$ |
| Example 11 | 6 | $6.93\ 10^{-6}$ | $1.13\ 10^{-6}$ | $0.28 < DE_{50} < 4.59$ |
| Example 12 | 5 | $5.87\ 10^{-4}$ | $3.19\ 10^{-5}$ | |
| Example 13 | 5 | $8.42\ 10^{-5}$ | $7.15\ 10^{-6}$ | |
| Example 14 | 6 | $3.86\ 10^{-4}$ | $1.38\ 10^{-5}$ | |
| Example 15 | 5 | $4.54\ 10^{-5}$ | $6.12\ 10^{-6}$ | |
| Example 16 | 5 | $1.23\ 10^{-5}$ | $3.49\ 10^{-6}$ | |
| Example 17 | 5 | $2.22\ 10^{-6}$ | $4.5\ 10^{-7}$ | $0.11 < DE_{50} < 1.79$ |
| Example 18 | 5 | $8.37\ 10^{-6}$ | $9.4\ 10^{-7}$ | $0.165 < DE_{50} < 5.37$ |
| Example 19 | 5 | $2.36\ 10^{-5}$ | $2.36\ 10^{-6}$ | $0.32 < DE_{50} < 17.63$ |
| Example 20 | 5 | $3.46\ 10^{-6}$ | $8.7\ 10^{-7}$ | $0.19 < DE_{50} < 4.0$ |
| Example 21 | 5 | $3.89\ 10^{-6}$ | $1.0\ 10^{-6}$ | $0.28 < DE_{50} < 3.56$ |
| Example 22 | 4 | $3.51\ 10^{-6}$ | $7.3\ 10^{-7}$ | $0.16 < DE_{50} < 3.39$ |
| Example 23 | 5 | $7.4\ 10^{-7}$ | $1.8\ 10^{-7}$ | $0.048 < DE_{50} < 0.645$ |

TABLE II-continued

Effect of the compounds of the invention on coronary tension induced by $PFG_{2\alpha}$

| Products tested | Number of experiments | $DE_{20}$ (M) | $DE_{50}$ (M) | Confidence interval $[10^{-6}M]$ |
|---|---|---|---|---|
| Example 24 | 4 | $2.41\ 10^{-5}$ | $9.9\ 10^{-7}$ | $0.067 < DE_{50} < 14.56$ |
| Example 25 | 5 | $>>10^{-4}$ | $3.7\ 10^{-4}$ | $0.008 < DE_{50}$ |
| Example 26 | 5 | $4.53\ 10^{-5}$ | $7.67\ 10^{-6}$ | $1.00 < DE_{50} < 58.78$ |
| Example 27 | 5 | $>>10^{-4}$ | $>>10^{-4}$ | |
| Example 28 | 5 | $>>10^{-4}$ | $1.96\ 10^{-4}$ | $0.02 < DE_{50}$ |
| Example 29 | 5 | $>>10^{-4}$ | $>>10^{-4}$ | |
| Example 30 | 5 | $7.39\ 10^{-5}$ | $1.04\ 10^{-5}$ | $0.90 < DE_{50} < 119.4$ |
| Reference products | | | | |
| Efloxate | 7 | $3.58\ 10^{-5}$ | $3.94\ 10^{-6}$ | $0.94 < DE_{50} < 16.54$ |
| Dipyridamole | 6 | $1.61\ 10^{-6}$ | $4.46\ 10^{-7}$ | $0.2 < DE_{50} < 0.99$ |
| R05-4864 | 9 | $9.38\ 10^{-6}$ | $1.48\ 10^{-6}$ | $0.6 < DE_{50} < 3.62$ |
| PK 11195 | 7 | $9.13\ 10^{-6}$ | $1.66\ 10^{-6}$ | $0.63 < DE_{50} < 4.35$ |
| Diazepam | 7 | $1.64\ 10^{-5}$ | / | $0.99 < DE_{50} < 7.10$ |

C) Conclusions

The results above show that we are dealing with compounds which combine with the so-called peripheral sites for benzodiazepines and relax coronary smooth muscle. The selectivity of action of these compounds for the smooth muscle, and more particularly the vascular smooth muscle leads to important therapeutic application in the treatment of acute anginal crisis, the prophylactic treatment of angina pectoris crisis and postischemic treatment, in obliterative arteriosclerosis and peripheral vasodilation in bronchial diseases and asthma.

We claim:

1. A compound selected from imidazo[1,2-c]quinazolines of the formula I:

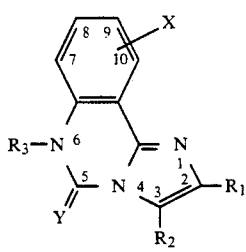

(I)

in which:
Y represents oxygen or sulfur;
$R_1$ represents:
a) alkyl having 1 to 6 carbon atoms, optionally substituted by phenyl optionally mono- or disubstituted by halogen or alkyl or alkoxy having 1 to 6 carbon atoms;
b) mono-, bi- or tricyclic cycloalkyl having 3 to 10 carbon atoms;
c) an aromatic group chosen from among:
phenyl and phenyl mono- or disubstituted by halogen or alkyl or alkoxy having 1 to 6 carbon atoms, and
furyl and thienyl, or
d) alkoxycarbonyl, aminocarbonyl or N,N-dialkylaminocarbonyl, in which alkyl has 1 to 6 carbon atoms, or benzoyl optionally mono- or disubstituted by halogen atom or alkyl or alkoxy having 1 to 6 carbon atoms;

$R_2$ represents hydrogen or halogen or alkyl having 1 to 6 carbon atoms optionally substituted by amino, alkylamino or dialkylamino in which alkyl has 1 to 6 carbon atoms;

$R_3$ represents:
a) hydrogen,
b) alkyl radical having 1 to 6 carbon atoms, optionally substituted by phenyl optionally mono- or polysubstituted by alkyl or alkoxy having 1 to 6 carbon atoms, or
c) a radical of formula:

R—CO—A— in which:
A is alkylene having 1 to 6 carbon atoms, and
R is alkoxy having 1 to 6 carbon atoms or an amino radical of formula:

in which R' and R", identical or different, each represent hydrogen or alkyl having 1 to 6 carbon atoms optionally substituted by hydroxyl or alkoxy having 1 to 6 carbon atoms, or R' and R" form, together with the nitrogen atom to which they are attached, a saturated 5 or 6 membered heterocyclic radical optionally containing a second hetero atom selected from oxygen and nitrogen, remaining ring atoms being carbon,
d) phenyl, optionally substituted by one or more alkyl or alkoxy having 1 to 6 carbon atoms;

X represents hydrogen or halogen, and pharmacologically-acceptable acid addition salts thereof.

2. A physiologically tolerated salt of a compound of claim 1 with a pharmacologically-acceptable acid.

3. Compound of claim 1 being 2-Ethoxycarbonyl-6-benzyl-5-oxo-5,6-dihydroimidazo[1,2-c]quinazoline.

4. Compound of claim 1 being 2-Phenyl-6-N,N-diethylaminocarbonylmethyl-5-oxo-5,6-dihydroimidazo[1,2-c]quinazoline.

5. Compound of claim 1 being 2-(p-Methoxyphenyl)-6-N,N-diethylaminocarbonylmethyl-5-oxo-5,6-dihydroimidazo[1,2-c]quinazoline.

6. Compound of claim 1 being 2-Phenyl-6-(N-methyl-N-phenylacetamido)-5-oxo-5,6-dihydroimidazo[1,2-c]quinazoline.

7. Compound of claim 1 being 2-Phenyl-6-N,N-dipropylaminocarbonylmethyl-5-oxo-5,6-dihydroimidazo[1,2-c]quinazoline.

8. Compound of claim 1 being 2-(m-Chlorophenyl)-3-methyl-6-N,N-dipropylaminocarbonylmethyl-5-oxo-5,6-dihydroimidazo[1,2-c]quinazoline.

9. A pharmaceutical composition useful for treating coronary smooth-muscle dysfunction containing as active principle a compound as claimed in claim 1 together with a pharmaceutically-acceptable carrier.

10. A method for treating a living animal afflicted with a coronary smooth muscle dysfunction, comprising the step of administering to the said living animal an amount of a compound of claim 1 which is effective for alleviation of the said conditions.

* * * * *

UNITED STATES PATENT AND TRADEMARK OFFICE
CERTIFICATE OF CORRECTION

PATENT NO. : 5,128,338

DATED : Jul. 7, 1992

INVENTOR(S) : Jean-Jacques Bourguignon, Camille-Georges Wermuth, Jean-Francois Renaud de la Faverie, Catherine Thollon, Alain Lombet It is certified that error appears in the above-identified patent and that said Letters Patent is hereby corrected as shown below:

Column 2, approximately line 21; "example, phenyl" should read -- example, a phenyl --.
Column 10, line 41; "0 65" should read --0.65--.
Column 11, approximately line 16; "1.41 t," should read -- 1.41: t, --.
Column 12, approximately line 47,48; "6---N," should read -- 6-N, --.
Column 13, line 4-5; "methyl---5-" should read --methyl-5- --.
Column 13, approximately line 46; "EXAMPLE 4" should read -- Example 45: --.
Column 18, line 40; "physiologically tolerated" should read -- physiologically-tolerated --.
Column 18, line 67; "conditions." should read -- condition. --.

Signed and Sealed this

Thirty-first Day of August, 1993

Attest:

BRUCE LEHMAN

Attesting Officer

Commissioner of Patents and Trademarks